United States Patent [19]
Li Mutti et al.

[11] 4,127,502
[45] Nov. 28, 1978

[54] STABILIZERS FOR RECONSTITUTED, LYOPHILIZED SAMPLES

[75] Inventors: Charles M. Li Mutti, Hilton; Tai-Wing Wu; Shirley Y. Lynn, both of Rochester, all of N.Y.

[73] Assignee: Eastman Kodak Company, Rochester, N.Y.

[21] Appl. No.: 805,507

[22] Filed: Jun. 10, 1977

[51] Int. Cl.$^2$ ............................................. G01N 33/16
[52] U.S. Cl. ................................. 252/408; 23/230 B
[58] Field of Search ....................... 23/230 B; 252/408

[56] References Cited

U.S. PATENT DOCUMENTS

| | | | |
|---|---|---|---|
| 3,260,648 | 7/1966 | Fox | 23/230 B |
| 3,413,198 | 11/1968 | Deutsch | 195/63 X |
| 3,682,835 | 8/1972 | Louderback | 23/230 B X |
| 3,751,381 | 8/1973 | Megraw | 23/230 B X |
| 3,753,925 | 8/1973 | Louderback et al. | 23/230 B X |
| 4,040,785 | 8/1977 | Kim et al. | 23/230 B |

*Primary Examiner*—Morris O. Wolk
*Assistant Examiner*—Arnold Turk
*Attorney, Agent, or Firm*—Dana M. Schmidt

[57] ABSTRACT

A serum matrix or serum-derived composition which, after lyophilization and reconstitution, has a reduced optical density, evidencing improved homogeneity.

12 Claims, No Drawings

STABILIZERS FOR RECONSTITUTED, LYOPHILIZED SAMPLES

BACKGROUND OF THE INVENTION (1) Field of the Invention

This invention relates to a serum matrix or serum-derived composition containing lipids, such as a lipid calibrator, which has been stabilized against inhomogeneity which results from lyophilization and reconstitution with water.

(2) State of the Prior Art

Automated clinical analyzers such as those which rely upon radiometric detection of a change in absorption require calibration using a "standard" calibrator. Such calibrators permit two or more known concentrations of an analyte of choice to be fixed at particular levels, e.g., color densities, as read by the analyzer, and from these a curve is derived for use with readings of unknown analyte concentrations.

For example, lipid calibrators are used for calibrating the analysis of cholesterol and triglycerides. Such calibrators, as with other calibrators, are either prepared fresh on a daily basis, or as is more common, are stored in a lyophilized condition for reconstitution at a later date. It is well-known that lipoproteins will not readily tolerate lyophilization, but rather produce an inhomogeneous, turbid reconstituted solution, due to instability of particular lipoproteins to the lyophilization process. Serum and blood plasma containing lipoproteins and glucose in naturally occurring amounts have also demonstrated unacceptable turbidity after lyophilization and reconstitution.

U.S. Pat. Nos. 3,260,648 issued on July 12, 1966 and 3,955,925 issued on May 11, 1976 are illustrative of the problem. As explained in these patents, turbidity interferes with the analysis and therefore with the calibration of the analyzer. Although turbidity might be overcome by many-fold dilutions, such dilutions are time-consuming and therefore undesirable.

U.S. Pat. Nos. 3,955,925 and 4,011,045; and Japanese Patent O.P.I. No. 144724/76 are of interest, because they disclose that turbidity upon lyophilization and reconstitution can be avoided, by removing, such as by salting out, most of the lipoproteins which are the primary cause of the turbidity problem. Thereafter, desired proteins such as α-fetoprotein, which is not a lipoprotein, or glycerides of low molecular weight fatty acids, are added back. In the Japanese process, lactose is described as a useful additive for the lyophilization step, presumably for the bulking effect described hereinafter. The technique described in U.S. Pat. No. 4,011,045 however is seemingly of limited utility, being disclosed as a method for preparing a useful standard only for triglycerides.

Because fresh, daily preparation of the calibrator is usually impractical as an alternative to lyophilization and reconstitution, what is needed is an additive that will permit the reconstitution of lyophilized lipid calibrators without a significant loss of optical clarity.

Sugar and sugar derivatives have been used as bulking agents and stabilizers for reconstituted, lyophilized assay mixtures, as shown for example in U.S. Pat. No. 3,413,198. However, the assay mixtures described in this patent are not disclosed specifically as containing lipids such as cholesterol or triglyceride, and no recognition is given to an improvement in clarity to be achieved by the use of such "bulking agents."

Lactose has been used as a bulking agent for solutions in general to be lyophilized, but only where the solutions require such bulk for ease in the lyophilization process. However, the amounts of lactose used for this effect generally have been less than that found to be effective by this invention to provide clarity. Moreover, lipoproteins due to their large molecular size do not require such additional bulking agents.

Glucose is of course a sugar that is both naturally present in serum or has been added to calibrators of various kinds. However, the amount present either naturally or by addition has been ineffective to produce any clarity stabilization, as is evident from the fact that human serum, upon lyophilization, typically exhibits a drastic increase in turbidity.

Patents which relate generally to the background of lipids or other calibrators include U.S. Pat. Nos. 3,274,062; issued on Sept. 20, 1966; 3,751,381 issued Aug. 7, 1973; 3,897,363 issued July 29, 1975; and 4,007,008 issued Feb. 8, 1977.

OBJECTS OF THE INVENTION

It is an object of this invention to provide a lipid-containing serum matrix or serum composition which upon lyophilization and reconstitution has a homogeneity which is superior to that which results in such processing of untreated serum or serum matrices.

It is another object of the invention to provide such a matrix or composition with a homogeneity, at the user's option, which is comparable to that of the matrix or composition prior to lyophilization.

It is a related object of the invention to provide a lipid calibrator with a homogeneity as described above, even after lyophilization and reconstitution.

Other objects and advantages will become apparent upon reference to the following Summary and Detailed Description.

SUMMARY OF THE INVENTION

The invention concerns a serum matrix or serum-derived composition which, upon lyophilization and reconstitution, has a homogeneity that is superior to what is obtained from lyophilization and reconstitution of untreated serum matrices and serum-derived compositions. Such improved homogeneity is readily measured in terms of the reduced optical density of the reconstituted matrix or composition.

More specifically, in accordance with one aspect of the invention there is provided a stabilized serum matrix or serum-derived composition comprising lipids and a clarity stabilizer comprising a sugar, sugar amine, or sugar alcohol in at least an amount sufficient to reduce the optical density of the composition, after lyophilization and reconstitution with water, below the optical density of said lyophilized and reconstituted matrix or composition lacking said stabilizer, when measured at 700 nm.

This composition has a preferred utility as a lipid calibrator.

There is further provided, by this invention, a method of maintaining homogeneity in a lipid-containing serum matrix or serum-derived composition even after lyophilizing and reconstituting, comprising the steps of (a) adding to said matrix or composition prior to lyophilization a clarity stabilizer comprising a sugar, sugar amine, or sugar alcohol in at least an amount sufficient to reduce the optical density of the composition, after lyophilization and reconstitution with water, below the optical density of said lyophilized and reconstituted matrix or composition lacking said stabilizer, when measured at 700 nm; and (b) thereafter lyophilizing said matrix or composition; whereby upon reconstitution with water said matrix or composition has a reduced amount of turbidity.

DESCRIPTION OF THE PREFERRED EMBODIMENTS

Serum matrices and serum-derived compositions, which include serum as well as plasma, can be stored in powdered form. However, the lyophilization and reconstitution process may introduce substantial amounts of inhomogeneity. Such inhomogeneity is conveniently measured in terms of the turbidity of the liquid sample, and significant departures from optically clear levels are deemed to be evidence of such inhomogeneity. As used herein, "optically clear" means having an optical density no greater than about 0.5. All optical densities herein referred to are measured at a wavelength of 700 nm, a wavelength at which inherent absorption capabilities of serum will not interfere, and a 1 cm. path length.

It has been discovered that by the use of clarity stabilizers, serum matrices and serum-derived compositions can be lyophilized and reconstituted with a retention of homogeneity beyond that available for matrices and compositions not processed in accordance with the invention. Such serum matrices or serum-derived compositions of the invention can be in liquid or lyophilized form, and if liquid, can be derived or reconstituted from the lyophilized form.

Thus, in one form of the invention a clarity stabilizer is added to the serum matrix or serum-derived composition in at least an amount which is sufficient to measurably reduce the optical density, and therefore the inhomogeneity, measured after lyophilization and reconstitution, to a level below that which would occur in the absence of the stabilizer. As used herein, "measurably reduce" means a reduction in optical density of at least about 0.5.

In another form of the invention, the amounts of stabilizer can be increased to levels which produce an optical density, and therefore a homogeneity, that is comparable to that of the freshly prepared matrix or composition, in liquid form, prior to lyophilization. As used herein, "comparable" means producing an optical density which is increased, if at all, compared to the unlyophilized matrix or composition lacking the stabilizer, by no more than about 0.5, measured at 700 nm.

In still another form of the invention, the clarity stabilizers are present in maximum amounts which provide a matrix or composition, after lyophilization and reconstitution, that is optically clear, i.e., has an absolute optical density no greater than about 0.5, at 700 nm.

The particular level of optical density, and therefore homogeneity, that is selected from among the aforedescribed three levels will depend of course on the amount of inhomogeneity that the user can tolerate in his clinical analysis procedure. Analysis procedures most sensitive to turbidity and inhomogeneity may require the use of an optically clear matrix. But even the most insensitive procedures can benefit by the measurable reduction in optical densities achievable by this invention.

Although hereinafter described embodiments of the invention are directed to the preferred utility as a calibrator, other uses are contemplated. For example, the invention provides a means of converting fresh serum or a serum-derived composition to dry form for purposes of storage and then reconstituting it without substantially affecting the homogeneity of the fresh serum. The reconstituted serum matrix or serum-derived composition can then be used in any of a variety of different medical or clinical applications.

As is apparent, the optical density levels after reconstitution depend in part on the amount of water used. As used herein, "reconstitution" means the addition of water in an amount sufficient to restore the volume to what it was just prior to lyophilization, with no further dilutions. Thus, the amount of water used in the reconstitution is fixed by the amount that was present before.

The preferred utility of such compositions is as a lipid calibrator for clinical analysis. Also, for other assays, other analytes can be present in the calibrator in addition to lipids, as long as the other analytes and the clarity stabilizer are compatible, i.e., the analytes are not attacked or otherwise rendered undetectable in the assay of choice, by the clarity stabilizer. Thus, analytes such as blood urea nitrogen, electrolytes such as potassium and chloride, bilirubin, amylase, and the like can be present where compatible with the clarity stabilizer of choice. Such additional analytes are preferred and conventional where the calibrator is intended to be a broad reference calibrator for a number of different individual analytes. Of course, if the calibrator is being used in an analysis for glucose, a clarity stabilizer other than glucose would normally be selected.

Clarity stabilizers which have been found to be effective in this invention include sugars, sugar alcohols and sugar amines. Useful examples of these classes include glucose, sucrose, lactose, arabinose, sorbitol, fructose, xylitol, mannitol, and glucosamine. It is further contemplated that any sugar, sugar alcohol, or sugar amine apart from those just named will also be effective if used in appropriate amounts. Of course, with some sugars or sugar derivatives, there is an upper limit as to the amount that can be used, as excess amounts become insoluble. As will be appreciated, the level at which insolubility occurs depends upon the particular stabilizer and matrix to which it is added.

The amount which will render the clarity of the reconstituted composition comparable to that of the material prior to lyophilization depends largely upon which clarity stabilizer is selected. Typically, an effective amount has been found to range between about 2.5 to about 30 grams per deciliter of solution. It will be appreciated that these amounts can vary slightly depending upon the level of lipids, or upon further optimization of the matrix. Also, the amounts selected can vary slightly depending upon the amount of protein.

The stabilizers described above can be used to stabilize any lipid-containing composition which is to be lyophilized and later reconstituted. Highly preferred uses feature the addition of the stabilizers to human serum matrices for any use in general, and for lipid calibrators in particular.

The present invention is applicable to a serum matrix or serum-derived composition obtained from any of a wide variety of sources, including conventional calibrator suppliers such as commercially available cholesterol concentrates or pooled human serum. The lipids can be obtained from these sources, or from nonserum sources such as egg yolk. A useful technique in preparing calibrators comprises column separation of lipids from pooled human serum by exclusion chromatography followed by further concentration of the lipid-containing column fractions using ultrafiltration, optional dilution of the concentrate to lower lipid values, if desired, and optional dialysis to replace the eluant fluid with a salt solution of desired constituents. More specifically, column separation comprises loading conventional gel permeation chromatographic columns with human serum from any source, and using a buffered solution to elute the large lipoproteins from the serum while retaining albumin in the column. A buffered solution is preferred because of the possibility of denaturing the lipoproteins if the pH is allowed to vary drastically. Typical buffered solutions which are useful include those having a pH between about 7 and about 8, such as 0.1 M Tris buffer or Ringer's solutions prepared with this specific pH. The desired lipid-containing eluant coming off the column may still be too low in lipid concentration, about 50 to 100 mg/dl total cholesterol, so that further concentration may be desired for the higher lipid levels needed in calibrators. A highly preferred concentration technique includes conventional ultrafiltration using for example an ultrafiltration cell equipped so that molecules with a molecular weight greater than 5000 daltons are retained.

Detection of the presence and/or amount of lipids in the lipid-rich fractions from the column can be done by any conventional assay technique, such as the Liebermann-Burchard or the Zak assays. Alternatively, the cholesterol detection element described in *Research Disclosure*, Vol. 126, October 1974, No. 12626, published by Industrial Opportunities Limited, Homewell, Havant Hampshire PO91EF, United Kingdom, can be used.

Upon reaching the highest lipid concentration desired, dilutions to lower concentrations for a multipoint calibrator can be achieved by adding the stock concentrate to pooled human serum, if desired. Furthermore, the level of proteins can be adjusted, if desired, by adding back gamma globulin and/or albumin.

Dialysis of the resultant lipid-containing liquid is a further optional and conventional processing step, particularly if the eluant does not contain the desired salts. A Ringer's solution or any isotonic salt solution, containing sodium chloride and optionally other ions such as potassium, is particularly useful for this purpose. Such other ions are desirable in preparing, for example, an ion-selective electrode calibrator.

EXAMPLES

The invention can be further illustrated by the following representative examples. All optical densities (O.D.) expressed herein are in terms of the relationship O.D. = log $I_o/I$, wherein $I_o$ is the intensity of the incident ray and I is the intensity of the transmitted ray. The wavelength of the incident ray was, in all instances, 700nm.

Examples 1-4

The stabilizers listed in Table I were added at various levels to aliquots of column-generated lipid concentrate containing about 500mg/dl total cholesterol, about 450 mg/dl triglycerides and about 4 g/dl total protein containing essentially no albumin. This concentrate was prepared by eluting lipid-rich fractions from human serum added to a 30 l. Pharmacia column filled with Sephadex G-200, the eluant being 0.1 M Tris buffer containing 0.1 M sodium chloride. After elution, the fractions were combined and ultrafiltered using a filter having a molecular weight cutoff at 5000 daltons, and dialyzed against a physiologic saline solution containing 8.5 g/dl NaCl. The examples and a control containing no stabilizer were lyophilized and subsequently reconstituted with distilled water. A measure of turbidity was obtained by noting the optical densities of the reconstituted examples on a Beckman 25 Spectrophotometer, at 700nm. Results are shown in Table I, the control being shown both before and after lyophilization and reconstitution.

Table I

| Example | Stabilizer | Stabilizer Amount (g/dl) | Optical Density |
| --- | --- | --- | --- |
| Control-unlyophilized | none | 0 | 0.50 |
| Control-lyophilized & reconstituted | none | 0 | >2.9 |
| 1 - lyophilized & reconstituted | arabinose | 2.5 | 2.5 |
|  | arabinose | 5.0 | 1.08 |
|  | arabinose | 15.0 | 0.6 |
| 2 - lyophilized & reconstituted | sorbitol | 2.5 | 2.6 |
|  | sorbitol | 5.0 | 1.53 |
|  | sorbitol | 15.0 | 0.52 |
| 3 - lyophilized & reconstituted | sucrose | 2.5 | 2.7 |
|  | sucrose | 5.0 | 1.63 |
|  | sucrose | 15.0 | 0.51 |
| 4 - lyophilized & reconstituted | glucosamine | 2.5 | 2.6 |
|  | glucosamine | 5.0 | 1.34 |
|  | glucosamine | 15.0 | 1.15 |

Table I demonstrates that, for the matrix tested, the amounts required for comparable clarity were, for arabinose, about 5 g/dl; for sorbitol and for sucrose, about 10g/dl, and for glucosamine, about 15 g/dl. The amounts required to create an optically clear standard, found to exist in the control prior to lyophilization, were, for arabinose, sorbitol, and sucrose, about 15 g/dl.

Examples 5-10

The procedures of Examples 1-4 were repeated, except that the serum matrix was pooled human serum obtained from Interstate Blood Bank, which contained about 390 mg/dl triglycerides, 219 mg/dl total cholesterol, and about 7 g/dl protein as determined by the Biuret procedure, of which at least about half was albumin. The concentrations of the stabilizers were varied as shown in Table II, and the optical densities measured after lyophilization and reconstitution only, except for the control which was measured before as well as after lyophilization and reconstitution.

TABLE II

| Example | Stabilizer | Stabilizer Amount (g/dl) | Optical Density |
|---|---|---|---|
| Control-unlyophilized | none | 0 | 0.396 |
| Control-lyophilized & reconstituted | none | 0 | >2.50 |
| 5 - lyophilized & reconstituted | glucose | 5.0 | >2.50 |
|  | glucose | 10.0 | 0.808 |
|  | glucose | 20.0 | 0.295 |
| 6 - lyophilized & reconstituted | lactose | 5.0 | >2.50 |
|  | lactose | 10.0 | insoluble |
| 7 - lyophilized & reconstituted | arabinose | 5.0 | >2.50 |
|  | arabinose | 10.0 | 0.697 |
|  | arabinose | 20.0 | 0.267 |
| 8 - lyophilized & reconstituted | mannitol | 10.0 | >2.50 |
|  | mannitol | 20.0 | insoluble |
| 9 - lyophilized & reconstituted | fructose | 5.0 | >2.50 |
|  | fructose | 10.0 | 0.941 |
|  | fructose | 20.0 | 0.467 |
|  | fructose | 30.0 | 0.174 |
| 10 - lyophilized & reconstituted | glucosamine | 10.0 | >2.50 |
|  | glucosamine | 20.0 | insoluble |

These results demonstrated that, for the matrix tested, the amounts of glucose, arabinose, and fructose necessary for clarity comparable to that of the unlyophilized control were about 10 g/dl. Glucose, arabinose and fructose all produced optically clear standards useful as lipid calibrators when 20 g/dl were used. In fact, both arabinose at 20 g/dl and fructose at 30 g/dl demonstrated after reconstitution a clarity that was superior even to the clarity of the matrix prior to lyophilization.

The failure in these examples of lactose, mannitol, and glucosamine, at these levels, particularly when compared with Examples 1-4, most likely can be explained on the basis of the increased protein levels of this matrix.

Example 11

The following example demonstrates that the reductions in optical densities obtainable by the invention are in fact a measure of a lack of inhomogeneity of the type evidenced by turbid, lyophilized and reconstituted lipoprotein materials available from prior art techniques.

Analytical data was obtained on the serum components cholesterol, glucose, total proteins and uric acid from pooled human serum that was (1) fresh, (2) lyophilized without a clarity stabilizer and (3) lyophilized with 5 g/dl sorbitol and reconstituted. Table III shows that with the additive the matrix or composition provides a highly repeatable analysis compared to the lyophilized matrix without an additive, such as is desirable for a calibrator.

The invention has been described in detail with particular reference to certain preferred embodiments thereof, but it will be understood that variations and modifications can be effected within the spirit and scope of the invention.

What is claimed is:

1. A stabilized serum matrix or serum-derived composition comprising
    lipids,
    and a clarity stabilizer comprising a sugar, sugar amine, or sugar alcohol in at least an amount sufficient to measurably reduce the optical density of the composition, after lyophilization and reconstitution with water, below the optical density of said lyophilized and reconstituted matrix or composition lacking said stabilizer, when measured at 700 nm. using a 1 cm. path length.

2. A composition as defined in claim 1, wherein said stabilizer is present in an amount sufficient to maintain the optical density of the composition, after lyophilization and reconstitution with water, at a level comparable to the optical density of said composition prior to lyophilization, when measured at about 700 nm. using a 1 cm. path length.

3. A composition as defined in claim 2, wherein said stabilizer is present in an amount sufficient to render the reconstituted composition optically clear.

4. A stabilized serum matrix or serum-derived composition comprising
    lipids,
    and a clarity stabilizer selected from the group consisting of glucose, sucrose, lactose, arabinose, sorbitol, fructose, xylitol, mannitol, and glucosamine;
    said stabilizer being present in at least an amount sufficient to measurably reduce the optical density of the composition, after lyophilization and recon- Table III Assay Values of Selected Serum Analytes in a Human Serum Pool

| | Untreated Matrix | | | | | | Stabilized Matrix (5 g/dl Sorbitol) | | |
|---|---|---|---|---|---|---|---|---|---|
| | Unlyophilized Control | | | Lyophilized and Reconstituted Without Stabilizer | | | Lyophilized and Reconstituted With Water | | |
| Analyte Assayed[1] | Average mg/dl (n=3) | Std Dev (σ) | % COV[2] | Average mg/dl (n=3) | Std Dev (σ) | % COV | Average mg/dl (n=3) | Std Dev (σ) | % COV |
| Total Cholesterol (Gilford) | 205.53 | 0.58 | 0.28 | 203.3 | 14.47 | 7.12 | 199.3 | 0.58 | 0.29 |
| Glucose (ACA DuPont) | 136.3 | 3.79 | 2.78 | 136.3 | 1.15 | 0.85 | 138.33 | 0.58 | 0.43 |
| Total Protein (ACA) | 6.40 | 0.00 | 0.00 | 6.25 | 0.01 | 0.09 | 6.8 | 0.0 | 0.0 |
| Uric Acid (ACA) | 6.73 | 0.06 | 0.86 | 6.47 | 0.21 | 3.22 | 6.67 | 0.15 | 2.29 |

[1] The name within the parentheses indicates the assay used.
[2] Throughout this table, COV stands for Coefficient of Variation.

stitution with water, below the optical density of said lyophilized and reconstituted matrix or composition lacking said stabilizer, when measured at 700 nm. using a 1 cm. path length.

5. A composition as defined in claim 4, wherein said stabilizer is present in an amount sufficient to maintain the optical density of the composition, after lyophilization and reconstitution with water, at a level comparable to the optical density of the matrix or composition prior to lyophilization, when measured at about 700 nm. using a 1 cm. path length.

6. A serum assay standard, comprising
a lipid selected from cholesterol, cholesterol esters and triglyceride;
and a clarity stabilizer comprising a sugar, sugar amine, or sugar alcohol in at least an amount sufficient to measurably reduce the optical density of the standard, after lyophilization and reconstitution with water, below the optical density of said lyophilized and reconstituted standard lacking said stabilizer, when measured at 700nm. using a 1 cm. path length.

7. A standard as defined in claim 6, wherein said stabilizer is present in an amount sufficient to maintain the optical density of the standard, after lyophilization and reconstitution with water, at a level comparable to the optical density of the matrix or composition prior to lyophilization, when measured at about 700 nm. using a 1 cm. path length.

8. A standard as defined in claim 7, wherein said stabilizer is present in an amount sufficient to render the reconstituted standard optically clear.

9. A serum assay standard comprising
a lipid selected from cholesterol, cholesterol esters, and triglyceride;
and a clarity stabilizer selected from the group consisting of glucose, sucrose, lactose, arabinose, sorbitol, xylitol, mannitol, and glucosamine;
said stabilize being present in at least an amount sufficient to measurably reduce the optical density of the standard, after lyophilization and reconstitution with water, below the optical density of said lyophilized and reconstituted standard lacking said stabilizer, when measured at 700 nm. using a 1 cm. path length.

10. A standard as defined in claim 9, wherein said stabilizer is present in an amount sufficient to maintain the optical density of the standard, after lyophilization and reconstitution with water, at a level comparable to the optical density of the matrix or composition prior to lyophilization, when measured at about 700 nm. using a 1 cm. path length.

11. A standard as defined in claim 10, wherein said stabilizer is present in an amount sufficient to render the reconstituted standard optically clear.

12. In a method of maintaining homogeneity in a lipid-containing serum matrix or serum-derived composition, wherein said matrix or composition is lyophilized and then reconstituted; the improvement comprising the step of
adding to said matrix or composition prior to the lyophilization step, a clarity stabilizer comprising a sugar, sugar amine, or sugar alcohol in at least an amount sufficient to measurably reduce the optical density of the composition, after lyophilization and reconstitution with water, below the optical density of said lyophilized and reconstituted matrix or composition lacking said stabilizer, when measured at 700 nm. using a 1 cm. path length;
whereby upon reconstitution with water said matrix or composition has a reduced amount of turbidity.

* * * * *

UNITED STATES PATENT AND TRADEMARK OFFICE
CERTIFICATE OF CORRECTION

PATENT NO. : 4,127,502
DATED : November 28, 1978
INVENTOR(S) : Charles M. LiMuti et al.

It is certified that error appears in the above-identified patent and that said Letters Patent are hereby corrected as shown below:

Column 9, line 10, "700nm." should read --- 700 nm. ---.

Column 10, line 4, "said stabilize being" should read --- said stabilizer being ---.

Signed and Sealed this

Third Day of July 1979

[SEAL]

Attest:

LUTRELLE F. PARKER

Attesting Officer     Acting Commissioner of Patents and Trademarks